United States Patent
Langhauser et al.

Patent Number: 5,457,171
Date of Patent: Oct. 10, 1995

[54] CATALYST SYSTEMS FOR THE POLYMERIZATION OF $C_2$-$C_{10}$-ALKENES

[75] Inventors: Franz Langhauser, Mutterstadt; Martin Lux, Dannstadt-Schauernheim; Rolf Muelhaupt, Freiburg; David Fischer, Denzlingen, all of Germany

[73] Assignee: BASF Aktiengesellschaft, Ludwigshafen, Germany

[21] Appl. No.: 284,441
[22] PCT Filed: Jan. 30, 1993
[86] PCT No.: PCT/EP93/00211
§ 371 Date: Aug. 3, 1994
§ 102(e) Date: Aug. 3, 1994
[87] PCT Pub. No.: WO93/16116
PCT Pub. Date: Aug. 19, 1993

[30] Foreign Application Priority Data

Feb. 10, 1992 [DE] Germany ............ 42 03 753.0

[51] Int. Cl.[6] ............ C08F 4/609; C08F 10/00
[52] U.S. Cl. ............ 526/132; 502/125; 526/133; 526/351
[58] Field of Search ............ 502/125; 526/131, 526/132

[56] References Cited

U.S. PATENT DOCUMENTS 5,354,721 10/1994 Geerts ............ 526/133

FOREIGN PATENT DOCUMENTS 348126 12/1989 European Pat. Off. .
444474 9/1991 European Pat. Off. .
92/01005 1/1992 WIPO .

Primary Examiner—Edward J. Smith
Attorney, Agent, or Firm—Keil & Weinkauf

[57] ABSTRACT

Catalyst systems for the polymerization of $C_2$-$C_{10}$-alkenes contain, as active components, a metallocene complex of a metal of subgroup IV or V of the Periodic Table, an oligomeric alumina compound and a cyclic boron compound of the general formula IV

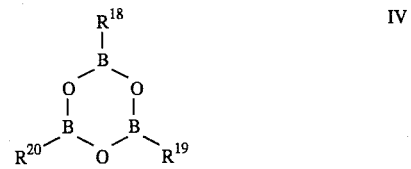

where $R^{18}$ to $R^{20}$ are each $C_1$-$C_{10}$-alkyl which may be monosubstituted to trisubstituted by halogen, $C_6$-$C_{15}$-aryl or $C_1$-$C_{10}$-alkoxy, $C_4$-$C_7$-cycloalkyl which may be monosubstituted to trisubstituted by halogen, $C_1$-$C_{10}$-alkyl or $C_1$-$C_{10}$-alkoxy, $C_1$-$C_{10}$-alkoxy which may be monosubstituted to trisubstituted by halogen, $C_1$-$C_{10}$-alkyl or $C_6$-$C_{15}$-aryl, or $C_6$-$C_{15}$-aryl which may be monosubstituted to pentasubstituted by halogen, $C_1$-$C_{10}$-alkyl or $C_1$-$C_{10}$-alkoxy.

5 Claims, No Drawings

CATALYST SYSTEMS FOR THE POLYMERIZATION OF $C_2$-$C_{10}$-ALKENES

The present invention relates to catalyst systems for the polymerization of $C_2$-$C_{10}$-alkenes, containing, as active components, metallocene complexes of metals of subgroups IV and V of the Periodic Table, an oligomeric alumina compound and a cyclic boron compound of the formula IV

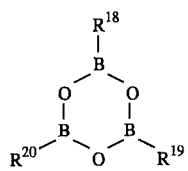

where
$R^{18}$ to $R^{20}$ are each $C_1$-$C_{10}$-alkyl which may be monosubstituted to trisubstituted by halogen, $C_6$-$C_{15}$-aryl or $C_1$-$C_{10}$-alkoxy, $C_4$-$C_7$-cycloalkyl which may be monosubstituted to trisubstituted by halogen, $C_1$-$C_{10}$-alkyl or $C_1$-$C_{10}$-alkoxy, $C_1$-$C_{10}$-alkoxy which may be monosubstituted to trisubstituted by halogen, $C_1$-$C_{10}$-alkyl or $C_6$-$C_{15}$-aryl, or $C_6$-$C_{15}$-aryl which may be monosubstituted to pentasubstituted by halogen, $C_1$-$C_{10}$-alkyl or $C_1$-$C_{10}$-alkoxy.

The present invention furthermore relates to the use of such catalyst systems for the preparation of polyalkenes and processes for the preparation of polyalkenes with the aid of these catalyst systems.

For the polymerization of olefins with metallocene catalysts, a large excess of oligomeric alumina compounds is required in order to ensure high productivities of the catalyst systems, as is disclosed, for example, in EP-A 444 474. A large excess of aluminum leads to high residual aluminum content in the polymer products, which may have a disadvantageous effect in the processing or necessitates expensive purification steps for the polymer.

WO 92/01005 and EP-A 348 126 describe the preparation of alumoxane compounds by reacting boroxines with trialkylaluminum compounds. WO 92/01005 also discloses a catalyst for the polymerization of olefins which consists of a metallocene and the alumoxane compounds prepared by the abovementioned process. EP-A 348 126 furthermore describes the use of the alumoxane compounds prepared by the abovementioned process as a component in a catalyst system which consists of metallocene and alumoxane compounds and is used in the preparation of polyethylene.

It is an object of the present invention to provide catalyst systems in which the amount of oligomeric alumina compounds can be reduced or which, with the same amount of oligomeric alumina compounds, have a higher productivity and hence permit more economical preparation of polyalkenes.

We have found that this object is achieved by the catalyst systems defined at the outset for the preparation of polyalkenes. We have also found the use of such catalyst systems for the preparation of polyalkenes and processes for the preparation of polyalkenes with the aid of these catalyst systems.

Among the active components, the novel catalyst systems contain one or more complexes of metals of subgroups IV and V of the Periodic Table, in particular of titanium, zirconium, hafnium, vanadium, niobium or tantalum. Preferably used complexes are those in which the metal atom is bonded via $\pi$ bonds to unsaturated cyclic hydrocarbon radicals, for example cyclopentadienyl, fluorenyl or indenyl groups. Furthermore, in the preferably used complexes the metal atom may also be bonded to further ligands, in particular to fluorine, chlorine, bromine and iodine or to $C_1$-$C_{10}$-alkyl, for example methyl, ethyl, propyl or butyl. Particularly suitable complexes contain in particular chlorine.

Particularly useful complexes are of the formula I

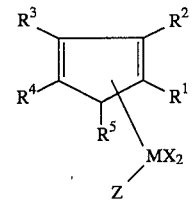

where
M is titanium, zirconium, hafnium, vanadium, niobium or tantalum, X is fluorine, chlorine, bromine, iodine, hydrogen, $C_1$-$C_{10}$-alkyl, $C_6$-$C_{15}$-aryl or —$OR^6$, $R^6$ is $C_1$-$C_{10}$-alkyl, $C_6$-$C_{15}$-aryl, alkylaryl, arylalkyl, fluoroalkyl or fluoroaryl, where each alkyl radical is of 1 to 10 carbon atoms and each aryl radical is of 6 to 20 carbon atoms, $R^1$ to $R^5$ are each hydrogen, $C_1$-$C_{10}$-alkyl, 5-membered to 7-membered cycloalkyl which in turn may carry $C_1$-$C_{10}$-alkyl as a substituent, $C_6$-$C_{15}$-aryl or arylalkyl, where two adjacent radicals together may furthermore form a cyclic group of 4 to 15 carbon atoms, or $Si(R^7)_3$, $R^7$ is $C_1$-$C_{10}$-alkyl, $C_6$-$C_{15}$-aryl or $C_3$-$C_{10}$-cycloalkyl,

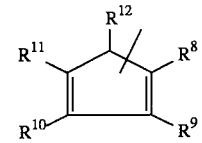

$R^8$ to $R^{12}$ are each hydrogen, $C_1$-$C_{10}$-alkyl, 5-membered to 7-membered cycloalkyl which in turn may carry $C_1$-$C_{10}$-alkyl as a substituent, $C_6$-$C_{15}$-aryl or arylalkyl, and two adjacent radicals together may furthermore form a cyclic group of 4 to 15 carbon atoms, or $Si(R^{13})_3$, $R^{13}$ is $C_1$-$C_{10}$-alkyl, $C_6$-$C_{15}$-aryl or $C_3$-$C_{10}$-cycloalkyl, or $R^4$ and Z together form a group —$[Y(R^{14})_2]_n$—E—, Y is silicon, germanium, tin or carbon, $R^{14}$ is $C_1$-$C_{10}$-alkyl, $C_3$-$C_{10}$-cycloalkyl or $C_6$-$C_{10}$-aryl, n is 1, 2, 3 or 4,

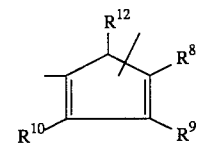

$R^{15}$ is $C_1$-$C_{10}$-alkyl, $C_6$-$C_{15}$-aryl, $C_3$-$C_{10}$-cycloalkyl, alkylaryl or $Si(R^{16})_3$ and $R^{16}$ is $C_1$-$C_{10}$-alkyl, $C_6$-$C_{15}$-aryl, $C_3$-$C_{10}$-cycloalkyl or alkylaryl.

Among the metallocene complexes of the general formula I,

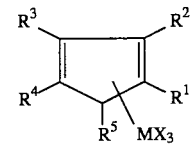

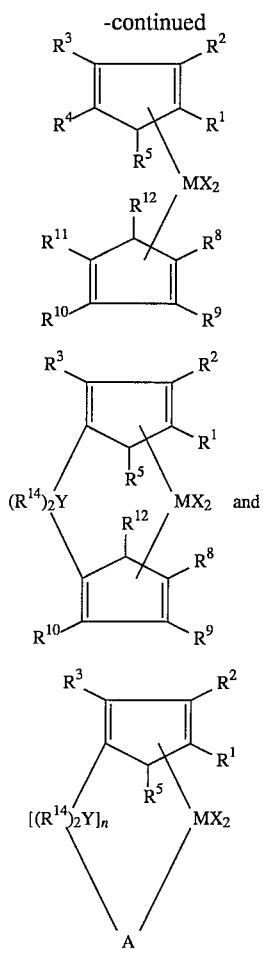

are preferred.

The term metallocenes is thus understood as meaning not only the bis(η-cyclopentadienyl)-metal complexes.

Particularly preferred compounds of the formula Ia are those in which

M is titanium, zirconium or hafnium, X is chlorine and $R^1$ to $R^5$ are each hydrogen or $C_1$-$C_4$-alkyl.

Preferred compounds of the formula Ib are those in which

M is zirconium or hafnium, X is chlorine, $C_1$-$C_4$-alkyl or phenyl, $R^1$ to $R^5$ are each hydrogen, $C_1$-$C_4$-alkyl or $Si(R^7)_3$ and $R^8$ to $R^{12}$ are each hydrogen, $C_1$-$C_4$-alkyl or $Si(R^{13})_3$.

Particularly suitable compounds of the formula Ib are those in which the cyclopentadienyl radicals are identical, the unsubstituted cyclopentadienyl radicals being preferred.

Examples of particularly suitable compounds include bis(cyclopentadienyl)zirconium dichloride, bis(pentamethylcyclopentadienyl)zirconium dichloride, bis(cyclopentadienyl)diphenylzirconium, bis(methylcyclopentadienyl)zirconium dichloride, bis(ethylcyclopentadienyl)zirconium dichloride, bis(n-butylcyclopentadienyl)zirconium dichloride and bis(trimethylsilylpentadienyl)zirconium dichloride and the corresponding dimethylzirconium compounds.

Particularly suitable compounds of the formula Ic are those in which $R^1$ and $R^8$ are identical and are each hydrogen or $C_1$-$C_{10}$-alkyl, $R^5$ and $R^{12}$ are identical and are each hydrogen, methyl, ethyl, isopropyl or tert-butyl, $R^3$ and $R^{10}$ are each $C_1$-$C_4$-alkyl, $R^2$ and $R^9$ are each hydrogen or two adjacent radicals $R^2$ and $R^3$ or $R^9$ and $R^{10}$ together form a cyclic group of 4 to 12 carbon atoms, $R^{14}$ is $C_1$-$C_8$-alkyl, M is zirconium or hafnium, Y is silicon, germanium, tin or carbon and X is chlorine.

Examples of particularly suitable complexes include dimethylsilanediylbis(cyclopentadienyl)zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylene-9-fluorenylcyclopentadienylzirconium dichloride, dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis(3-tert-butyl-5-methylcyclopentadienl)-dimethylzirconium, dimethylsilanediylbis(2-methylindenyl)zirconium dichloride, dimethylsilanediylbis(2-isopropylindenyl)zirconium dichloride, dimethylsilanediylbis(2-tert-butylindenyl)zirconium dichloride, diethylsilanediylbis(2-methylindenyl)zirconium dibromide, dimethylsilanediylbis(2-methyl-5-methylcyclopentadienyl)zirconium dichloride, dimethylsilanediylbis(2-ethyl-5-isopropylcyclopentadienyl)zirconium dichloride, dimethylsilanediylbis(2-methylindenyl)zirconium dichloride, dimethylsilanediylbis(2-methylbenzindenyl)zirconium dichloride and dimethylsilanediylbis(2-methylindenyl)-hafnium dichloride.

Particularly suitable compounds of the general formula Id are those in which

M is zirconium or hafnium, X is chlorine or $C_1$-$C_{10}$-alkyl, Y is silicon or carbon if n is 1 or is carbon is n is 2, $R^{14}$ is $C_1$-$C_8$-alkyl, $C_5$- or $C_6$-cycloalkyl or $C_6$-$C_{10}$-aryl,

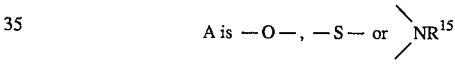

and $R^1$ to $R^3$ and $R^5$ are each hydrogen, $C_1$-$C_{10}$-alkyl, $C_3$-$C_{10}$-cycloalkyl $C_6$-$C_{15}$-aryl or $Si(R^7)_3$, or two adjacent radicals form a cyclic group of 4 to 12 carbon atoms.

Such complexes can be synthesized by conventional methods, the reaction of the correspondingly substituted, cyclic hydrocarbon anions with halides of titanium, zirconium, hafnium, vanadium, niobium or tantalum being preferred.

Examples of corresponding preparation processes are described in, inter alia, J. Organometal. Chem. 369 (1989), 359–370.

μ-Oxo-bis(chlorobiscyclopentadienyl)zirconium can also be used as the metallocene complex.

In addition to the metallocene complexes, the novel catalyst systems also contain oligomeric aluminum compounds.

For example, open-chain or cyclic alumoxane compounds of the formula II or III

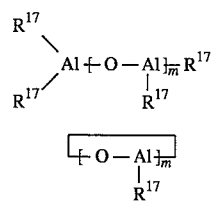

where $R^{17}$ is $C_1$-$C_4$-alkyl, preferably methyl or ethyl, and m is an integer of from 5 to 30, preferably from 10 to 25, are suitable.

The preparation of these oligomeric alumoxane compounds is usually carried out by reacting a solution of trialkylaluminum with water and is described in, inter alia, EP-A 284 708 and U.S. Pat. No. 4,794,096.

As a rule, the oligomeric alumoxane compounds obtained are in the form of mixtures of both linear and cyclic chain molecules of different lengths, so that m is to be regarded as an average value. Alumoxane compounds may also be present as a mixture with other metal alkyls, preferably with alkylaluminums.

Furthermore, the novel catalyst systems also contain cyclic boron compounds of the formula IV

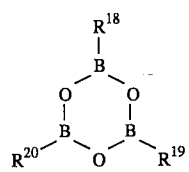

IV where $R^{18}$ to $R^{20}$ are each branched or, preferably, linear $C_1$-$C_{10}$-alkyl, preferably linear $C_1$-$C_4$-alkyl, in particular methyl or ethyl, which may be monosubstituted to trisubstituted by halogen, in particular fluorine or chlorine, $C_6$-$C_{15}$-aryl, preferably phenyl, or $C_1$-$C_{10}$-alkoxy, preferably $C_1$-$C_4$alkoxy; $C_4$-$C_7$-cycloalkyl, preferably $C_5$- or $C_6$-cycloalkyl, which may be monosubstituted to trisubstituted by halogen, in particular fluorine or chlorine, branched or, preferably, linear $C_1$-$C_{10}$-alkyl, preferably $C_1$-$C_4$-alkyl, or branched or, preferably, linear alkoxy of 1 to 10, in particular 1 to 4, carbon atoms; branched or, preferably, linear alkoxy of 1 to 10, preferably 1 to 4, carbon atoms which may be monosubstituted to trisubstituted by halogen, in particular fluorine or chlorine, branched or, preferably, linear $C_1$-$C_{10}$-alkyl, preferably $C_1$-$C_4$-alkyl, or $C_6$-$C_{15}$-aryl, preferably phenyl; $C_6$-$C_{15}$-aryl, preferably phenyl, which may be monosubstituted to pentasubstituted by halogen, preferably fluorine or chlorine, branched or, preferably, linear $C_1$-$C_{10}$-alkyl, in particular $C_1$-$C_4$-alkyl, or branched or, preferably, linear alkoxy of 1 to 10, in particular 1 to 4, carbon atoms.

Compounds of the formula IV in which all three radicals $R^{18}$, $R^{19}$ and $R^{20}$ have the same meaning have proven particularly suitable.

The unsubstituted compounds are preferred in each case, and $R^{18}$ to $R^{20}$ are each in particular unsubstituted linear $C_1$-$C_4$-alkyl or $C_6$-$C_{10}$-aryl groups. Triethylboroxine and dimethylboroxine are particularly preferred.

The preparation of cyclic boron compounds of the general formula IV is known per se to the skilled worker and can be carried out, for example, by reacting boron oxide with trialkylboranes, as disclosed, for example, in U.S. Pat. No. 5,001,244.

Mixtures of different cyclic boron compounds of the general formula IV may also be used.

It has proven advantageous if the atomic ratio of aluminum from the oligomeric alumina compound to the metal of subgroup IV or V of the Periodic Table from the metallocene complex is from 10:1 to $10^6$:1, preferably from 10:1 to $10^4$:1.

The atomic ratio of the boron from the cyclic boron compound of the general formula IV to aluminum from the oligomeric alumina compound may be from $10^{-4}$:1 to 1:1, preferably from $10^{-2}$:1 to 1:1, in particular from 0.05:1 to 0.2:1.

The three components of the novel catalyst systems may be introduced into the polymerization reactor individually in any order or as mixtures.

With the aid of these catalyst systems, it is possible to prepare polymers of alkenes. These are understood as meaning homo- and copolymers of $C_2$-$C_{10}$-alkenes, preferably $C_2$-$C_{10}$-alk-1-enes, the monomers used preferably being ethylene, propylene, but-1-ene, pent-1-ene and hex-1-ene.

The preparation of these polymers can be carried out in the conventional reactors used for the polymerization of alkenes, either batchwise or, preferably, continuously. Suitable reactors include continuously operated stirred kettles, and, if required, a plurality of stirred kettles connected in series are also used.

In a preferred embodiment, the oligomeric alumoxane compound, preferably as a solution in an inert solvent, for example in benzene, toluene, hexane, heptane or a mixture thereof, is initially taken and is heated to 20°–100° C. The alkenes are then added, after which the polymerization is initiated by adding a mixture of the complex of metals of the subgroups IV and V of the Periodic Table and the cyclic boron compound, which are preferably also dissolved in an inert solvent, in particular in that in which the oligomeric alumoxane compound has been dissolved.

The polymerization conditions are not critical as such, pressures of from 0.5 to 3,000, preferably from 1 to 80, bar and temperatures of from −50° to +300° C., preferably from −20° to 100° C., being usual.

Polymerization reactions with the aid of the novel catalyst systems can be carried out in the gas phase, in a suspension, in liquid monomers and in inert solvents. In the polymerization in solvents, in particular liquid hydrocarbons such as benzene or toluene are used. Polymers having good performance characteristics can also be obtained in the polymerization in the gas phase, in a suspension or in liquid monomers.

The novel catalyst systems have very high productivity, and the polymers prepared with the aid of said systems have a low content of catalyst residues and a narrow molecular weight distribution.

EXAMPLES

Preparation of Polypropylene (PP)

EXAMPLE 1

600 ml of dry toluene and 1.74 g ($\triangleq$30 mmol of Al) of methylalumoxane as a 30% strength by weight solution in toluene were initially taken in a 2 l glass autoclave and heated to 40° C., and propylene was passed in until the total pressure had reached 2 bar. Polymerization was initiated by the addition of 1.26 mg ($\triangleq$0.003 mmol) of rac.-ethylenebis(1-indenyl)zirconium dichloride and 188 mg (1.5 mmol) of trimethylboroxine in 15 ml of toluene. The temperature and pressure were kept constant at 40° C. and 2 bar. After a reaction time of 3 hours, the polymerization was terminated by letting down the pressure in the reactor, and a mixture of 1.5 l of methanol and 15 ml of concentrated HCl was added to the product. The polymer formed was washed with methanol and dried under reduced pressure.

EXAMPLE 2

The procedure was similar to that in Example 1, except that 600 ml of dry toluene and 0.87 g (15 mmol of Al) of methylalumoxane as a 30% strength by weight solution in toluene were initially taken. The polymerization was initiated by 8.77 mg ≙0.03 mmol) of bis(cyclopentadienyl)zirconium dichloride and 94 mg ≙0.75 mmol) of trimethylboroxine in 15 ml of toluene.

COMPARATIVE EXAMPLES V1 AND V2

The procedure was as in Examples 1 and 2, but without the addition of trimethylboroxine.

The yields and the properties of the polypropylenes are summarized in the Table.

The limiting viscosity numbers [η] were determined at 135° C. in decalin, the weight average molecular weight $M_w$, and the number average molecular weight $M_n$ in Example 1 and Comparative Example 1 by gel permeation chromatography, the number average molecular weight $M_n$ in Example 2 and Comparative Example 2 by determination of the terminal groups by $^{13}$C-NMR and the melting point $T_m$ by DSC (Differential Scanning Calorimetry) measurements.

TABLE

| Example | Atomic ratio of Al from methylalumoxane to Zr from complex | Atomic ratio of boron from trimethylboroxine to Al from methylalumoxane | PP | Yield [g] | [η] [dl/g] | $\bar{M}_w$ [g/mol] | $\bar{M}_n$ [g/mol] | $\bar{M}_w/\bar{M}_n$ | $T_m$ [°C.] |
|---|---|---|---|---|---|---|---|---|---|
| 1 | $10^4$:1 | 0.15:1 | isotactic | 144 | 0.40 | 41700 | 23200 | 1.8 | 135 |
| 2 | 500:1 | 0.15:1 | atactic | 205 | — | — | 500 | — | — |
| V1 | $10^4$:1 | — | isotactic | 46 | 0.36 | 36400 | 21400 | 1.7 | 133 |
| V2 | 500:1 | — | atactic | 68 | — | — | 280 | — | — |

We claim:

1. A catalyst system for the polymerization of $C_2$-$C_{10}$-alkenes, containing, as active components, a metallocene complex of metals of the subgroups IV and V of the Periodic Table, an oligomeric alumina compound selected from the group consisting of open-chain or cyclic alumoxane compounds of the formula II or III

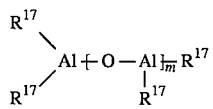   II

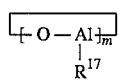   III where $R^{17}$ is $C_1$-$C_4$-alkyl and m is an integer of from 5 to 30 and a cyclic boron compound of the formula IV

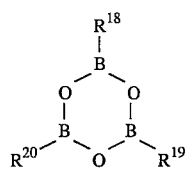   IV where $R^{18}$ to $R^{20}$ are each $C_1$-$C_{10}$-alkyl which may be monosubstituted to trisubstituted by halogen, $C_6$-$C_{15}$-aryl or $C_1$-$C_{10}$-alkoxy, $C_4$-$C_7$-cycloalkyl which may be monosubstituted to trisubstituted by halogen, $C_1$-$C_{10}$-alkyl or $C_1$-$C_{10}$-alkoxy, $C_1$-$C_{10}$-alkoxy which may be monosubstituted to trisubstituted by halogen, $C_1$-$C_{10}$-alkyl or $C_6$-$C_{15}$-aryl or $C_6$-$C_{15}$-aryl which may be monosubstituted to pentasubstituted by halogen, $C_1$-$C_{10}$-alkyl or $C_1$-$C_{10}$-alkoxy.

2. A catalyst system as claimed in claim 1, wherein the atomic ratio of aluminum from the oligomeric alumina compound to the metal of subgroup IV or V of the Periodic Table from the metallocene complex is from 10:1 to $10^6$:1.

3. A catalyst system as defined in claim 1, wherein the atomic ratio of boron from the cyclic boron compound of the formula IV to aluminum from the oligomeric alumina compound is from $10^{-4}$:1 to 1:1.

4. A catalyst system as defined in claim 1, wherein a metallocene complex of the formula I

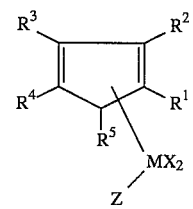   I where

M is titanium, zirconium, hafnium, vanadium, niobium or tantalum, X is fluorine, chlorine, bromine, iodine, hydrogen, $C_1$-$C_{10}$-alkyl, $C_6$-$C_{15}$-aryl or —$OR^6$, $R^6$ is $C_1$-$C_{10}$-alkyl, $C_6$-$C_{15}$-aryl, alkylaryl, arylalkyl, fluoroalkyl or fluoroaryl, where each alkyl radical is of 1 to 10 carbon atoms and each aryl radical is of 6 to 20 carbon atoms, $R^1$ to $R^5$ are each hydrogen, $C_1$-$C_{10}$-alkyl, 5-membered to 7-membered cycloalkyl which in turn may carry $C_1$-$C_{10}$-alkyl as a substituent, $C_6$-$C_{15}$-aryl or arylalkyl, where two adjacent radicals together may furthermore form a cyclic group of 4 to 15 carbon atoms, or $Si(R^7)_3$, $R^7$ is $C_1$-$C_{10}$-alkyl, $C_6$-$C_{15}$-aryl or $C_3$-$C_{10}$-cycloalkyl,

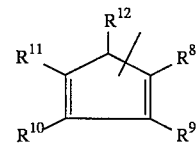

$R^8$ to $R^{12}$ are each hydrogen, $C_1$-$C_{10}$-alkyl, 5-membered to 7-membered cycloalkyl which in turn may carry $C_1$-$C_{10}$-alkyl as a substituent, $C_6$-$C_{15}$-aryl or arylalkyl, and two adjacent radicals together may furthermore form a cyclic group of 4 to 15 carbon atoms, or $Si(R^{13})_3$, $R^{13}$ is $C_1$-$C_{10}$-alkyl, $C_6$-$C_{15}$-aryl or $C_3$-$C_{10}$-cycloalkyl, or $R^4$ and Z together form a group —[Y($R^{14}$)$_2$]$_n$—E—, Y is silicon, germanium, tin or carbon, $R^{14}$ is $C_1$-$C_{10}$-alkyl, $C_3$-$C_{10}$-cycloalkyl or $C_6$-$C_{15}$-aryl, n is 1, 2, 3 or 4,

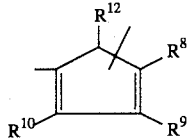

$R^{15}$ is $C_1$-$C_{10}$-alkyl, $C_6$-$C_{15}$-aryl, $C_3$-$C_{10}$-cycloalkyl, alkylaryl or $Si(R^{16})_3$ and $R^{16}$ is $C_1$-$C_{10}$-alkyl, $C_6$-$C_{15}$-aryl, $C_3$-$C_{10}$-cylcoalkyl or alkylaryl, is used as the metallocene complex of the metal of subgroup IV or V of the Periodic Table and an open-chain or cyclic alumoxane compound of the formula II or III

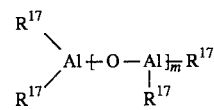 II

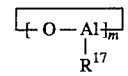 III where $R^{17}$ is methyl or ethyl and m is an integer of from 10 to 35, is used as the oligomeric alumina compound.

5. A process for the preparation of a polymer of $C_2$-$C_{10}$-alkenes at from 0.5 to 3000 bar and from −50° to +300° C. which comprises: contacting the alkenes with the catalyst system defined in claim 1.

* * * * *

UNITED STATES PATENT AND TRADEMARK OFFICE
CERTIFICATE OF CORRECTION

PATENT NO.: 5,457,171

DATED: October 10, 1995

INVENTOR(S): LANGHAUSER et al.

It is certified that error appears in the above-identified patent and that said Letters Patent is hereby corrected as shown below:

Column 8, claim 4, line 60, before the formula insert -- Z is X or --.

Column 9, claim 4, line 10, before the formula insert -- E is --.

Signed and Sealed this

Nineteenth Day of December, 1995

BRUCE LEHMAN

*Attest:*

*Attesting Officer*  *Commissioner of Patents and Trademarks*

UNITED STATES PATENT AND TRADEMARK OFFICE
CERTIFICATE OF CORRECTION

PATENT NO. : 5,457,171
DATED : October 10, 1995
INVENTOR(S) : Langhauser, et. al.

It is certified that error appears in the above-indentified patent and that said Letters Patent is hereby corrected as shown below:

Column 9, claim 4, after the formula, insert:

--or A, A is -O-, -S-, $\rangle NR^{15}$ or $\rangle PR^{15}$,--

Column 10, claim 4, last line, delete "to 35" and substitute -- to 25 --.

Signed and Sealed this

Twenty-sixth Day of August, 1997

Attest:

BRUCE LEHMAN

*Attesting Officer*        *Commissioner of Patents and Trademarks*